United States Patent [19]

Ali-Khan et al.

[11] Patent Number: 5,100,645
[45] Date of Patent: Mar. 31, 1992

[54] METHOD OF DIAGNOSIS OF AMYLOIDOSIS

[75] Inventors: Zafer Ali-Khan, Baie D'Urfé; Kamel Alizadeh-Khiavi, Montréal, both of Canada

[73] Assignee: Royal Institution for the Advancement of Learning (McGill Univ.), Montreal, Canada

[21] Appl. No.: 600,425

[22] Filed: Oct. 19, 1990

[51] Int. Cl.$^5$ .............................................. A61K 49/00
[52] U.S. Cl. ...................................................... 424/7.1
[58] Field of Search ......................................... 424/7.1

[56] References Cited

PUBLICATIONS

Saran, B. et al., Age 12(4):148 "Identification of Ubiquitin in the CSF of Young, Old, and AD Patients", Oct. 4-7, 1989.
Alizadeh-Khiavi, K. et al., Acta Neuropathol. (1991) 81: 280-286.
Chronopoulos, S. et al., J Pathol. (1991) 163: 199-203.
Chronopoulos, S. et al., J Pathol. 1991 "Ubiquitin: It's Potential Significance in Murine AA Amyloidogenesis".
Mann, D. et al., J Neurol. Neurosurg. Psychiatr. (1984) 47: 201-203.
Price, D. L. et al., Neuropep. Neurol. Psych. Disease (1986) Raven Press, N.Y. pp 209-213.

Katzman, R. et al., Neuropep Neurol Psych Disease (1986) Raven Press, N.Y. pp 279-286.
Suzuki, K. et al., J Neuropathol Exp Neurol (1965) 24: 211-224.
Jenkins, H. G. et al., J Neurochem 51(5): 1641-1645 (1988).

*Primary Examiner*—Frederick E. Waddell
*Assistant Examiner*—Diane Gardner
*Attorney, Agent, or Firm*—Goldsmith, Shore, Sutker & Milnamow, Ltd. Dressler

[57] ABSTRACT

In accordance with the present invention, there is now provided a method for the diagnosis of amyloidosis, which comprises subjecting a protein sample such as serum, cerebrospinal fluid or brain tissues containing amyloid deposits obtained from a patient suspected of suffering from an amyloidosis related disease to measurement of the amount of ubiquitin in said sample, and comparing the resulting amount with the amount of ubiquitin in a normal healthy patient. In a second aspect of the present invention, there is provided a method for the diagnosis of Alzheimer's disease, which comprises subjecting a protein sample obtained from the brain extract or cerebrospinal fluid of a patient suspected of suffering from Alzheimer's disease to measurement of the amount of ubiquitin, and comparing the resulting amount with the amount of ubiquitin in a normal healthy patient.

3 Claims, No Drawings

METHOD OF DIAGNOSIS OF AMYLOIDOSIS

TECHNICAL FIELD

The invention relates to a method for the diagnosis of amyloidosis and more particularly for the diagnosis of Alzheimer's disease.

PRIOR ART

Alzheimer's disease (AD) is an age-related human cerebral degenerative disease that is the most common cause of intellectual failure. Deterioration of memory and intellectual functions are believed to be a direct outcome of amyloid deposition in certain target sites in the brain. These deposits resulting from a disease process called amyloidosis, involve accumulation of fibrillar amyloid protein in the brain parenchyma in amounts sufficient to impair normal functions. Amyloid deposits involving cerebral blood vessels and the core of senile plaques, along with the generation of neurofibrillary tangles in selected cortical regions in the brain, are the cardinal lesions in Alzheimer's disease. Although senile plaques and neurofibrillary tangles in the brain are part of the "normal" aging process, the density and frequency of such lesions are much lower in "normal" aged humans. A majority of patients with Down's syndrome who live long enough to develop the additional brain disorder of senile dementia of Alzheimer type (SDAT), usually after age 40, exhibit similar neuropathological lesions characterized by senile plaques, neurofibrillary tangles and congophilic angiopathy. A definitive diagnosis of AD is made only by post mortem examination of brain tissues.

Secondary amyloidosis, a form of systemic amyloidosis in which non-neuronal tissues are involved, should be suspected when the condition of a patient with a chronic suppurative disease progressively deteriorates and some of the common manifestations of amyloidosis, such as hepatomegaly, splenomegaly, or albuminuria may appear. The prognosis for patients with generalized long-term amyloidosis is poor. Biopsy from target organs such as kidney, liver, heart, and the like, is the best screening test. Tissue sections are stained with Congo red dye and examined with a polarizing microscope for the demonstration of green birefringencent amyloid deposits.

Memory loss is the most prominent early symptom of Alzheimer's disease. Alzheimer's presenile and senile onset dementias are similar in both clinical and pathologic features, with the former commonly beginning in the 5th and 6th decades and the latter in the 7th and 8th decades, sometimes earlier, rarely later. The dementia usually progresses steadily, becoming well advanced in 2 to 3 years.

Over two million Americans have SDAT. It accounts for over 50% of the dementias in the elderly. About 60% of people in long-term care facilities have SDAT, and 20% of patients with Parkinson's disease develop this dementia. Multi-infarct dementia and SDAT coexist in about 15% of cases. SDAT is the fourth or fifth leading cause of death in Americans over 65 yr of age. It is seen more commonly in women perhaps because women live longer than men, but female gender may be a risk factor. SDAT increases in incidence with advancing age; e.g., less than 1% of individuals under 65 yr of age are affected, but 20% of those over 80 yr have some measure of dementia.

Early symptoms differ widely from patient to patient. The most common clinical picture is slow disintegration of personality and intellect due to impaired insight and judgement. Memory impairment increases, beginning with problems recalling recent events or remembering names; the impairment varies greatly from time to time and often from moment to moment. Remote memory impairment can be circumvented at first, but also is progressive as the defect increases.

One of the current most important problems of Alzheimer's disease is to find a reliable and accurate method of diagnosis of the disease. Diagnosis of Alzheimer's disease, so far, is a matter of clinical judgement. It is based on careful clinical history and mental status examination. A neuropsychologic diagnosis of Alzheimer-type dementia should not be accepted if the clinical evaluation is dubious, especially in patients who appear depressed or who may have other primary psychiatric disorders. Psychometric test results can be depended on only when the patient is freely communicative. Muteness of a failure to supply complete answers can result from depression as easily as from dementia. A consequence of this is that the clinical misdiagnosis of Alzheimer's disease is estimated to be approximately 20–30%.

It is therefore most important that a correct and early diagnosis be made in order to decide upon the best treatment. However, a definitive diagnosis of Alzheimer's disease is possible only on postmortem brain samples.

Therefore, it would be highly desirable to find a reliable, simple, less invasive method for the diagnosis of Alzheimer's disease. Such a test could then be performed on patients suspected of having Alzheimer's disease, even in the early stages.

SUMMARY OF THE INVENTION

In accordance with the present invention, there is now provided a method for the diagnosis of amyloidosis, which comprises subjecting a protein sample such as serum, cerebrospinal fluid or brain tissues containing amyloid deposits obtained from a patient suspected of suffering from an amyloidosis related disease to measurement of the amount of ubiquitin in said sample, and comparing the resulting amount with the amount of ubiquitin in a normal healthy patient.

In a second aspect of the present invention, there is provided a method for the diagnosis of Alzheimer's disease, which comprises subjecting a protein sample obtained from the brain extract or cerebrospinal fluid of a patient suspected of suffering from Alzheimer's disease to measurement of the amount of ubiquitin, and comparing the resulting amount with the amount of ubiquitin in a normal healthy patient.

DESCRIPTION OF THE INVENTION

Structural studies on purified amyloid proteins indicate at least 10 different chemical forms of human amyloids. The sharing of a number of common physical and staining characteristics by all amyloids suggests that there may be a common pathogenic factor in all forms of amyloidosis. The amyloid enhancing factor (AEF) is believed to be such a link. In fact, without the presence of a substantial tissue concentration of AEF, amyloid deposition does not occur.

AEF has been known for a long time, but its identification as ubiquitin has been discovered only recently. Based on the partial amino acid sequence homology, immunochemical and pathophysiological criteria, AEF activity in ubiquitin isolated and purified from murine amyloidotic tissues has been recently identified. Results prove that ubiquitin isolated from AD brain extracts also contain AEF activity and that both ubiquitin and AA amyloid (inflammation associated amyloid derived from serum amyloid A protein) codeposit in identical tissue sites in splenic perifollicular areas of mice undergoing accelerated amyloidogenesis.

Prior work on ubiquitin (Perry et al. Proc. Natl. Acad. Sci. U.S.A., 1987, 84, 3033) has shown that ubiquitin is found in association with highly insoluble neurofibrillary tangles (NFT) present both intracellularly in dystrophic neurones and in senile plaques in the brain. Based on spectral and ultrastructural characteristics, NFT have been classified as amyloid. However, neither the role of ubiquitin in the genesis of NFT, the intracellularly deposited amyloid, nor the quantitative aspect of ubiquitin related to Alzheimer's disease is described or mentioned.

Intracellularly, ubiquitin is found either free in a monomeric form, or linked via its COOH terminal glycine residue to $\epsilon$-$NH_2$ groups of lysine residues of a variety of cytoplasmic, nuclear and cell surface proteins.

The method of diagnosis of amyloidosis includes the following steps:
  obtaining a tissue biopsy sample or serum sample from a target organ of a patient suspected of suffering from amyloidosis related disease;
  extraction of soluble proteins present in the tissue sample; and
  measurement of the amount of ubiquitin in the extract or serum, and comparison with similar samples from age and sex matched "normal" patients.

The tissue extracts or serum obtained from patients suffering from amyloidosis can also be used in the mouse bioassay for the demonstration of increased and detectable levels of AEF activity.

As target organs, there may be mentioned liver, kidney, heart, and the like.

The method of diagnosis of Alzheimer's disease includes the following steps:
  obtaining a cerebrospinal fluid or brain biopsy sample from a patient suspected of suffering from Alzheimer's disease;
  extraction of soluble proteins present in the sample;
  measurement of the amount of ubiquitin in the cerebrospinal fluid or the tissue extract, and comparison with similar samples obtained from age and sex "matched" normal patients.

The brain extract or cerebrospinal fluid obtained from patients suffering from Alzheimer's disease, can also be used in the mouse bioassay for the demonstration of increased and detectable levels of AEF activity.

Depletion of and deterioration in enzyme activities during aging, a progressive intracellular accumulation of post-translationally altered proteins and a cumulative effect of oxidative stress are believed to trigger an increased synthesis of monomeric ubiquitin resulting in the intracellular accumulation of ubiquitinated altered proteins. Since ubiquitin is known to possess amyloid enhancing activity, the methods of the present invention were designed to quantitatively assess the levels of monomeric ubiquitin and ubiquitin bound to structural neuronal proteins in hippocampi from normal elderly and Alzheimer patients. Serum samples from mice which were undergoing inflammation-associated amyloidosis were used to measure the increased levels of ubiquitin in the sera.

Measurement of ubiquitin concentration by dot-blot assay

Age-associated neurodegenerative lesions such as paired helical filaments, senile plaques and congophilic angiopathy are infrequently seen in neurologically intact elderly humans. The density and frequency of these lesions, however, increase dramatically in the hippocampus, amygdala and cerebal cortex in patients with Alzheimer-type of dementia. Since Alzheimer brain derived monomeric ubiquitin manifests amyloid enhancing factor activity in mice, the experiments were designed to test the hypothesis whether cerebral amyloidosis in AD patients could be correlated with increased ubiquitin levels in the cortical brain extracts. The immunoblotting data based on the qualitative assessment of total ubiquitin in normal elderly and AD hippocampal preparation support the above hypothesis.

Similarly, since sera from amyloidotic mice on passive transfer induce accelerated splenic amyloidogenesis in the recipient mice, sera from mice undergoing amyloidogenesis have been tested, in order to evaluate levels of total ubiquitin prior and during amyloidogenesis.

The methods for the preparation of brain extracts, the generation of rabbit anti-bovine ubiquitin IgG antibody (RABU) and the dot-blot technique are described in the Examples. RABU is used for the demonstration of ubiquitin deposits in the mouse tissues undergoing amyloidogenesis, and measurement of the total amount of ubiquitin in the sera or brain extracts.

Although the antibody discussed in the present invention was obtained through standard polyclonal antibody procedures, it is to be appreciated that an anti-ubiquitin IgG antibody can also be obtained by standard monoclonal antibody procedures.

The following Examples are provided to illustrate the present invention rather than limit its scope.

EXAMPLE 1

Purification of Amyloid enhancing factor (or ubiquitin from AD brain extract)

Frozen ($-80°$ C.) coronal brain sections (18.6 g) from 3 Alzheimer's disease patients (male, 67 yrs, female, 86 yrs. and male, 79 yrs) were homogenized in 20 mM Tris-HCl, 1 mM EDTA, 5 mM 2-ME, 150 mM NaCl, pH 7.5 (10 ml/g) and centrifuged (30,000 g, 60 minutes, 4° C.). One half of the supernatant was treated with heat (90° C., 20 minutes) and the other half diluted (4.5:1) with 95% ethanol-chloroform (1:1; $-20°$ C.). The clarified supernatants were dialyzed (Spectrapor membrane, mol wt cut-off 3.5 kD) against distilled water and lyophilized. Each sample was treated similarly in the subsequent purification steps. The lyophilized brain extracts were dissolved in 25 mM Tris-HCl, pH 8 (T-buffer) and passed through a DEAE-Sepharose CL-6B column pre-equilibrated with T-buffer. The gel-bound proteins were eluted by a linear gradient of 100 mM NaCl in T-buffer. The flow through and the initial NaCl gradient eluted fractions were checked for the presence of ubiquitin, pooled, and subjected to gel filtration (Sephacryl S-200 HR column; 2.6×93 cm; flow rate 15 ml/h; preequilibrated in T-buffer). The resulting second peak, which contained almost all the monomeric ubiquitin was dialyzed against 50 mM ammonium acetate, pH 5, and passed through a CM-Sepharose column (preequilibrated in the dialyzing buffer). After the absorbance of the flow through at 280 nm reached the base line, the bound protein was eluted with 50 mM ammonium acetate, pH 6.4. Protein concentration was determined by using the Bio-Rad protein assay kit (Toronto, Ontario, Canada). Ubiquitin was purified to apparent homogeneity. Purification of ubiquitin was achieved by sequential chromatography of the crude brain extract on DEAE-Sepharose, Sephacryl S-200 HR, and CM-Sepharose. On a 15% SDS-polyacrylamide gel, the CM-Sepharose eluted purified AD-brain derived peptide had an apparent mol. wt of ~5.5 kDa. At most this peptide is present in trace amounts (approximately less than 1% of the total protein) in the crude extract, which demonstrated, on a 15% sodium dodecyl sulfate polyacrylamide gel electrophoresis gel (SDS-PAGE), approximately 37 peptides ranging in mol. wt between ~5.5 to >97.4 kDa.

On a 15% SDS-PAGE gel, the purified ~5.5 kDa peptide showed an identical electrophoretic mobility as that of bovine ubiquitin (BU). In Western immunoblotting both the ~5.5 kDa peptide, and BU, reacted with RABU. Immunostaining of these two peptides was abolished when RABU was absorbed with BU. Furthermore, partial amino acid sequence analysis of the ~5.5 kDa peptide from AD brain indicated a striking homology with murine AEF and eukaryotic ubiquitin. Ubiquitin, a highly conserved heat-shock or stress protein is present universally in all eukaryotic cells and it consists of a single 8.5 kDa polypeptide of 76 amino acid. However, due to abnormally high amounts of SDS binding, ubiquitin is known to manifest fast electrophoretic mobility in SDS-PAGE gel.

EXAMPLE 2

Mouse Bioassay for Determination of AEF activity;

The mouse bioassay technique for the determination of AEF activity is similar to that used for the demonstration of "human AEF" from amyloidotic human tissue extracts. Briefly, the crude AD brain extract as well as the AD-brain derived ubiquitin samples purified after heat treatment or ethanol-chloroform treatment of the crude brain extracts were dialyzed against PBS. As indicated in Table 1, some inocula contained 10 mM $CaCl_2$. Each mouse received either crude AD-brain extract or purified AD-brain derived ubiquitin (AD-Ub) or PBS with $CaCl_2$ i.p., and 4 daily s.c. injections of 0.5 ml of 1% $AgNO_3$. Mice were sacrificed 24 h after the last injection of $AgNO_3$, their spleens sectioned and stained with alkaline Congo red. Between 50 to 60 follicles from four Congo red-stained spleen sections were examined for congophilic green birefringent deposits. Amyloid deposition was graded between ± to 3+ depending upon the approximate splenic perifollicular (PFA) circumferential area covered with amyloid: ±, less than 10%; 1+, 10-25%; 2+, 25-50%; 3+, 50-100%. In subsequent mouse bioassay, mice were sacrificed 48 hours after the i.p. administration of either crude AEF or purified ubiquitin and one subcutaneous injection of 0.5 ml of 2% $AgNO_3$.

The mouse bioassay was used to determine AEF activity in the crude brain extract, and the two ~5.5 kDA peptide (heat-treated or ethanol-chloroform treated) preparations (Table 1). The crude extract showed potent AEF activity (group 1). Since addition of 10 mM $CaCl_2$ enhanced the AEF activity of purified murine ubiquitin, we next examined concentration-dependent amyloidogenic potency of the ~5.5 kD peptide isolates with or without $CaCl_2$. Ethanol-chloroform treated ~5.5 kDa peptide with added $CaCl_2$, at both 0.01 mg and 0.02 mg/mouse dosages, induced heavy amyloid deposition (Table 1, group 2). In sharp contrast, a 75% reduction was observed in the AEF potency when $CaCl_2$ was omitted from the highly amyloidogenic dosage (0.02 mg/mouse, Table 1, group 2). Interestingly, similar effect of $CaCl_2$ has been shown on the in vitro proteolytic activity of ubiquitin (Fried et al., Proc. Nat. Aca. Sci. USA, 84, 3685-3698). It was suggested that ubiquitin might function as a free protease and its activity might be regulated by $CaCl_2$.

Heat-treated ~5.5 kDa peptide, even with added $CaCl_2$, showed much reduced AEF activity (Table 1, group 3). When $CaCl_2$ was omitted from the heat-treated ~5.5 kDa peptide (0.2 mg/mouse) it failed to show AEF activity (group 3). Similar results were obtained with crude murine or AD brain tissue extracts exposed to heating, and also with the two ubiquitin preparations (murine and bovine) which were purified by exposing the crude extract to heat-treatment. In general, exposure of crude AEF to boiling abolishes most of the AEF activity.

TABLE 1

| Group | Crude brain extract or purified AEF | AEF Dosage mg/mouse | Diluent | 1% $AgNO_3$ injections | Number of mice* positive for AA/number examined | % of splenic follicles positive for AA | AA Grading |
|---|---|---|---|---|---|---|---|
| 1 | Whole extract | 1.0 | PBS | 4 | 3/3 | 82.9 ± 13.8 | 3+ |
| 2 | Purified AEF ethanol-chloroform-treated | 0.02 | PBS, 10 mM $CaCl_2$ | 4 | 3/3 | 100 | 3+ |
|   |   | 0.02 | PBS | 4 | 2/3 | 23.2 ± 10.6 | ± to 2+ |
|   |   | 0.01 | PBS, 10 mM $CaCl_2$ | 4 | 3/3 | 100 | 3+ |
| 3 | Purified AEF (heat-treated) | 0.2 | PBS, 10 mM $CaCl_2$ | 4 | 3/3 | 46.6 ± 7.3 | 1+ to 3+ |
|   |   | 0.2 | PBS | 4 | 0/3 | — | — |
|   |   | 0.01 | PBS, 10 mM $CaCl_2$ | 4 | 2/3 | 48.6 ± 10.8 | 1+ to 3+ |
| 4 | Controls | — | PBS, $CaCl_2$ | 4 | 0/3 | — | — |

*AA amyloid

EXAMPLE 3

Antibody (anti-bovine ubiquitin and anti-mouse AA amyloid antibodies)

The method for the purification of mouse AA amyloid and the generation of anti-AA antibody are well known in the art. The antiserum was passed through a Protein A-Sepharose gel column and rabbit anti-AA amyloid IgG antibody (RAA) was eluted following the manufacturers instructions (Pharmacia, Montreal, Canada).

The method for the generation of rabbit anti-bovine ubiquitin IgG (RABU) is as follows: bovine ubiquitin (BU; 3.8 mg; Sigma Chemical Co., MO, U.S.A.) cross-linked to keyhole limpet hemocyanin (15 mg; Calbiochem, CA, U.S.A.) with 80 µl of 3% glutaraldehyde was used as the antigen (1:1 with Freund's complete adjuvant) to immunize rabbits. The antiserum was incubated (overnight, 4° C.) with CNBr-activated Sepharose 4B (Pharmacia, Montreal, Canada) conjugated to BU (5 mg protein/ml gel) and the bound protein was eluted from the gel with 0.1M glycine-HCl, pH 2.8. The eluted protein was dialyzed against 0.1M sodium phosphate buffer pH 7.4, containing 0.5M NaCl and passed through a Protein A-Sephrose gel column to elute RABU. Both RAA and RABU were dialyzed against 0.01M phosphate buffer pH 7.4 containing 0.15M NaCl (PBS) and their protein concentrations determined as described above. For control experiments these antibodies were absorbed, overnight at 4° C., with their respective antigens in the following proportions: 5 mg of BU with 0.2 mg of RABU or 20 µg purified mouse AA amyloid with 4 µg of RAA. The absorbed antisera were microfuged for 15 minutes at 4° C. and the supernatants used for assessing the specificity of the immunostaining reactions.

EXAMPLE 4

Histochemical and immunocytochemical assays for the demonstration of ubiquitin and amyloid deposits Cryostat spleen sections (8 µm) were stained with Congo red for the demonstration of amyloid deposits in murine tissues. For immunostaining, the sections were fixed in acetone (10 min), washed in TTBS (20 mM Tris, 150 mM NaCl, 0.2% Tween 20, pH 7.5) twice for 5 minutes and then incubated in 3.3% $H_2O_2$ in methanol for 30 minutes to quench endogenous peroxidase. After washing in TTBS, the sections were incubated with 10% normal horse serum (NHS) in TTBS, washed twice for 5 minutes in 5% NHS in TTBS (used in subsequent washing steps and dilution of the primary and secondary antibodies and the strepavidinhorseradishperoxidase complex) and incubated in turn with the following: RAA (3 mg protein/ml, 1:800 dilution, overnight) or RABU (0.3 mg protein/ml; 1:640 dilution, overnight), biotinalated donkey anti-rabbit IgG (1:100 dilution, 60 minutes) and strepavidin-peroxidase complex (1:100 dilution, 60 minutes; Biotin-Strepavidin peroxidase kit was purchased from Amersham, Toronto, Canada). The sections were washed twice for 5 minutes between each incubation step. Color reaction was developed with 0.005% $H_2O_2$ and 0.02% 3,3-diaminobenzidine in 0.5M Tris-HCl, pH 7.6 and the sections were counterstained with hematoxylin. RABU-treated spleen sections were counterstained with 1% thioflavin S dissolved in distilled water (5 minutes, room temp.). The preimmune rabbit sera, RABU absorbed with bovine ubiquitin or RAA absorbed with purified mouse AA protein, were used to established specificity of the immunostaining.

To examine the spatial relationship between ubiquitin and AA amyloid deposits in AD-Ub induced amyloidosis, mouse spleen sections, were first stained with RABU and then counterstained with thioflavin S to detect amyloid deposition. Light to dark brown RABU-positive deposits, were found both intracellularly but mainly interstitially in both the AA positive and AA negative splenic PFAs. No staining was observed when the AA positive spleen sections were treated with either the preimmune rabbit serum or RABU absorbed with ubiquitin. Thus, ubiquitin is found at sites or potential sites of AA deposition. Also noticeable was the gradient in the intensity of RABU-positive brown staining in the spleen parenchyma. It was relatively high in the PFA containing AA (as opposed to normal PFA) and decreased gradually towards the red pulp. In contrast, spleen sections from normal mice showed focal clusters of RABU-positive cells, adjacent to the trabeculae and no brown deposits were present in the PFA. This indicates that local ubiquitin concentrations in conjunction with tissue deposited SAA play a role in amyloid deposition.

EXAMPLE 5

Biological significance of ubiquitin in amyloidogenesis

It has been shown that mice stimulated only with AEF neither show elevations in their serum amyloid A protein (SAA), the putative precursor of AA amyloid, nor develop splenic amyloid. Aqueous $AgNO_3$, a potent inducer of serum SAA when injected together with murine crude or purified ubiquitin or AD brain extract, induces accelerated amyloidosis in the recipient mice. Congo red stained sections from mice injected with AD-Ub and $AgNO_3$ showed green birefringent amyloid deposits in the PFA. This is a major site of amyloid deposition in mice. The deposition was AA type as judged by the staining of spleen sections from the same tissue block, with RAA; the immunostaining was totally abolished when RAA absorbed with purified mouse AA protein was used. Therefore, the purified ~5.5 kDa AD-Ub exhibits amyloidogenic activity and crosses the species barrier. Spleen sections from control mice with 4 $AgNO_3$ injections only were negative for AA deposits.

EXAMPLE 6

Methods for Qualitative assessment of total ubiquitin concentration in hippocampal extracts from normal elderly and Alzheimer's disease patients.

Samples of hippocampi were sonicated in 20 mM Tris-HCl buffer, containing anti-proteases, pH 7.4. The sonicated suspensions were centrifuged (60 min., 15000 g, 4° C.) and the supernatants separated. The sediments were sonicated and washed at least twice by microfugation. The sediments were boiled in Laemmli's buffer (5 min., 95° C.) and centrifuged. Both the first supernatant and the second supernatant were immunoblotted for the qualitative estimation of ubiquitin.

Two changes were introduced here in the development of immunoblots. First, the nitrocellulose membrane (pore size 0.20 µ; Scheicher and Shuell, NH, U.S.A.), after electrotransfer of the proteins was first dried at 70° C. for 10 min and then autoclaved for 30 min at 121° C. Second, $^{125}I$ conjugated to donkey anti-rabbit IgG ($^{125}I$-DRG; specific activity $2.22 \times 10^5$ cpm/ml; Amersham, Toronto, Canada) diluted 1:1000 in TM buffer (50 mM Tris-HCl, 150 mM NaCl, 5% defatted milk powder, 0.02% Na-azide, pH 7.5) was used to immunochemically stain the monomeric and ubiquitin conjugates. The blots were exposed on X-OMATKODAK Diagnostic Fast Film (Picker International, U.S.A.) for 15 to 40 hr at −70° C., as required.

The results show that both the normal and AD hippocampal supernatants contain mainly monomeric ubiquitin and some ubiquitin adducts.

Judging from the density of $^{125}I$ binding to the high molecular weight structural neuronal proteins obtained after boiling of the sedimental hippocampal tissue, it is apparent that qualitatively a greater proportion of structural neuronal proteins are ubiquitinated in AD as compared to normal elderly hippocampi.

One of the clinical interpretations of these observations, based on the finding that ubiquitin has AEF activity and binds to and degrades abnormal proteins, is that ubiquitin is involved in the pathogenesis of neurofibrillary tangles and Alzheimer-type A4 amyloid deposits. Neurofibrillary tangles are one of the heavily ubiquitinated fibrillar proteins. Also, ubiquitin deposits have been demonstrated to bind to the A4 amyloid deposits.

EXAMPLE 7

Measurement of the amount of ubiquitin by dot-blot assay in cortical brain extracts from normal elderly and Alzheimer's disease (AD) patients.

The cortical crude brain extracts were prepared as described in Example 6. The solid phase radioimmunoassay using 96-well Bio-Dot microfilteration unit (Bio-Rad, Toronto, Canada), nitrocellulose membrane (same as above), RABU and $^{125}$I-DRG, were used to quantitate total Ub-conjugates in cortical brain extracts from AD and non-AD brain samples. 100 μl each of bovine ubiquitin (starting well 9.76 ng), AD and non-AD cortical extracts (starting well 1:80), in 2-fold serial dilutions, were placed in each well and allowed to pass through the membrane. The membranes were heated (70° C., 10 min), autoclaved, blocked in 3% gelatin in Tris-HCl buffer (60 min) and then incubated with RABU (10 μg/ml, 60 min) or RABU absorbed with bovine ubiquitin. The methods for immunochemical staining and development of autoradiograms were similar to those described for immunoblotting. Total ubiquitin levels in the brain samples were determined by densitometry of the resulting autoradiograms. Since the autoradiograms of the resulting $^{125}$I-labeled dots were evenly stained, 1-D analyst software on an IBM-AT was used to develop a standard curve based on doubling dilutions of monomeric bovine ubiquitin (purchased from Sigma Chemical, MO, U.S.A.). The lowest detectable level of monomeric ubiquitin, under the present experimental conditions, was 76 pg. A model 620 video Densitometer (Bio-Rad, Toronto, Canada) containing the Intel 8086 microprocessor and an IBMT-AT computer were used to quantitate total ubiquitin in the cortical extracts by densitometry at 600 nm of the resulting autoradiogram. They were compared to monomeric ubiquitin standards applied to the same filter as the cortical extracts.

The data presented in Table 2 clearly shows that the mean concentration of total ubiquitin in AD samples (patients 1 to 4) is 1.7 fold higher than that present in the normal brain extracts (mean concentration of 15.34 μg/ml vs 9 μg/ml respectively).

The difference in these two means, i.e. 6.34 μg is significant with a 95% confidence interval.

Finally, the data from both the qualitative (immunoblotting) and quantitative (dot-blot) assay methods indicate that the total ubiquitin concentration is elevated in AD brain extracts.

TABLE 2

| Sample | Age, Sex, Case History | μg Ubiquitin/ml[2] |
|---|---|---|
| 1 | Male, 88, early slope SDAT[1] | 16.2 ± 7.5 |
| 2 | Male, 87, moderately severe SDAT | 20.0 ± 3.2 |
| 3 | Male, 79, moderately severe case of | 20.1 ± 5.3 |

TABLE 2-continued

| Sample | Age, Sex, Case History | μg Ubiquitin/ml[2] |
|---|---|---|
| | SDAT | |
| 4 | Female, 88, severe case of SDAT | 12.8 ± 3.7 |
| 5 | Male, 92, congestive hear disease | 7.1 ± 1.2 |
| 6 | Male, 59, cardiac disease | 10.2 ± 1.3 |
| 7 | Male, 70, rectal cancer | 9.7 ± 1.5 |

[1]SDAT—senile dementia of Alzheimer type
[2]Micrograms of ubiquitin per ml of cortical brain extent (100 mg of brain tissue/ml of extract buffer)

EXAMPLE 8

To investigate whether serum ubiquitin levels increase during secondary amyloidosis, the measurement of the amount of ubiquitin was carried out on serum samples from groups of mice prior to and during amyloidogenesis.

The method for the measurement of the amount of ubiquitin is similar to that described in Example 7. Briefly, mice were bled and their sera separated. One part of serum sample was mixed with three parts of sample buffer (0.5M Tris-HCl, pH 6.8, glycerol, 10% sodium dodecyl sulfate, 2-mercaptoethanol and distilled water), boiled 5 minutes, centrifuged, and then further diluted to 10 fold with normal saline. 100 μl of this treated sera in 2-fold serial dilutions was applied to the membrane fitted in the Bio-Rad Bio-Dot microfiltration apparatus. Subsequent processing of the membrane bound serially diluted murine sera for the demonstration of total ubiquitin, was carried out as described in Example 7.

The results are presented in Table 3. The data shows that the average serum ubiquitin level doubles at four weeks post-infection. This increase is highly significant ($P < 0.05$).

These results clearly show that an increased serum ubiquitin level can be used as a reliable biochemical marker for the diagnosis of secondary amyloidosis, and consequently, Alzheimer's disease.

TABLE 3

| Group | # of mice | Time period post-infection | μg ubiquitin/ ml of serum (Mean ± SD) |
|---|---|---|---|
| 1 | 4 | normal (0-hour) | 8.5 ± 1.46 |
| 2 | 4 | 24 hours | 9.8 ± 2.35 |
| 3 | 4 | 3 - days | 10.5 ± 3.08 |
| 4 | 4 | 5 - days | 9.4 ± 2.6 |
| 5 | 4 | 7 - days | 8.8 ± 2.39 |
| 6 | 4 | 2 - weeks | 9.34 ± 1.08 |
| 7 | 4 | 4 - weeks | 15.2 ± 4.37 |

What is claimed is:

1. A method for the diagnosis of amyloidosis, which comprises subjecting a protein sample containing amyloid deposits obtained from a patient suspected of suffering from amyloidosis related disease, to measurement of the concentration of ubiquitin in said sample, wherein a concentration of at least 9 μg of ubiquitin per mL of protein sample reveals the presence of amyloidosis.

2. A method according to claim 1, wherein said protein sample is obtained from a brain extract or cerebrospinal fluid.

3. A method according to claim 1, wherein the measurement of the concentration of ubiquitin is achieved by solid phase dot-blot assay, wherein the total concentration of ubiquitin is obtained by the densitometric analysis of the autoradiogram resulting from said dot-blot assay.

* * * * *